United States Patent [19]

Jelly

[11] Plant 4,559

[45] Jul. 1, 1980

[54] RED ROSE SEEDLING NAMED HILTACO

[75] Inventor: Robert G. Jelly, Richmond, Ind.

[73] Assignee: E. G. Hill Co., Inc., Richmond, Ind.

[21] Appl. No.: 24,581

[22] Filed: Feb. 28, 1979

[51] Int. Cl.[2] ..... A01H 5/00

[52] U.S. Cl. ..... Plt./28

[58] Field of Search ..... Plt./28

*Primary Examiner*—Robert E. Bagwill

*Attorney, Agent, or Firm*—Charles W. Rummler

[57] ABSTRACT

A red floribunda rose for greenhouse culture for the production of cut flowers, this new plant being characterized by a very free growth habit and good winter productivity, the lustrous red color of its blooms with excellent keeping tendencies, the much reduced occurrence of blind wood, and the strong resistance of its foliage to mildew.

8 Drawing Figures

BACKGROUND OF THE NEW PLANT

This new rose plant originated as a seedling resulting from my crossing of "Little Leaguer" (U.S. Plant Pat. No. 2,623), as the seed parent, with "Mary De Vor", (U.S. Plant Pat. No. 2,838), at Richmond, Ind., in the Fall of 1971 with the object of eliminating the blind and mildew characteristics of its pollen parent while retaining the better characteristics of both parents. The first flowers appeared in the Spring of 1973 and extensive testing of the plant through repeated propagations by grafting, under my direction, at Richmond , Ind., and by budding at Livermore, Calif., has demonstrated that the distinctive characteristics of the plant hold true from generation to generation and appear to be firmly fixed.

DESCRIPTION OF THE DRAWING

My new rose plant is illustrated by the accompanying photographic drawing which, in full color, shows face views of a newly opened flower and a three-day opened flower, buds in two stages of opening, and specimens of foliage and wood, the color rendition of this drawing being as nearly true as it is reasonably possible to obtain by conventional photographic procedures.

DESCRIPTION OF THE NEW VARIETY

The following is a detailed description of my new rose cultivar based upon observations of plants grown in greenhouse at Richmond, Ind., in February 1977, the color designations being according to The R.H.S. Colour Chart (RHS) published by The Royal Horticultural Society of London, England, the Horticultural Colour Chart by Robert S. Wilson (W), and the Nickerson Color Fan (N).

THE PLANT

Origin: Seedling identified as No. 15-74 RS.

Parentage:

*Seed parent.*—Little Leaguer (U.S. Plant Pat. 2,623).

*Pollen parent.*—Mary De Vor (U.S. Plant Pat. 2,838).

Classification: Floribunda.

Type: Greenhouse plant for culture to produce cut flowers.

Form: Bush.

Growth: Moderately free and vigorous.

Habit: Upright and much branched.

Canes: Small to medium in diameter.

Main stems: Color — Spinach Green 0960/1 (W).

*Thorns.*—Few, and long to medium in length and slightly hooked downward from a narrow base. Color: Greyed-Orange 165B (RHS).

*Prickles and hairs.*—None.

Branches: Color — Yellow Green 146B (RHS).

*Thorns.*—Few, long to medium in length and almost straight with a very narrow base. Color: A shade of Red 47C (RHS).

*Prickles and hairs.*—None.

Foliage:

*Quantity.*—Normal.

*Form of leaves.*—Odd pinnate. Size: Moderately normal and medium.

*Leaflets.*—3, 5 and 7 in number. Shape: Ovoid with round base, acute apex and simply serrate margin. Color: Young leaves: Upper surface — Yellow Green 146A to Yellow Green 146C (RHS). Under surface — a shade from Greyed Purple 183C to Greyed Purple 185A (RHS). Mature leaves: Upper surface — a blend between Yellow Green 147A and Yellow Green 147B (RHS). Under surface — a variation of Greyed Green 191A and Greyed Green 191C (RHS). Also, when hand held, there is a slight tinge of Greyed Purple 187D that shows.

*Rachis.*—Upper side: Medium grooved and slightly prickly. Under side: Slightly prickly.

*Stipules.*—Long to medium in length, moderately wide, with points which are medium in length and turn outward at an angle of less than 45°.

THE BUD

Before calyx breaks:

*Size.*—Medium large.

*Form.*—Long pointed with conspicuous neck and with foliaceous appendages on the surface of the bud having slender bristle-like parts extending beyond the tip of the bud a distance equal to three-fourths or more of the bud length.

*Color.*—Scheeles Green 860/2 (W) at the base shading to Yellow Green 146B and Yellow Green 146A (RHS).

As the calyx breaks:

*Outside petal color.*—Chrysanthemum Crimson 824/1 (W) shaded to Greyed Purple 187C (RHS).

As first petals open:

*Bud size.*—Medium small.

*Bud form.*—Long pointed.

*Color of petal.*—Outside — Yellow 1C at the point of attachment blending immediately to Greyed Purple 185B (RHS). Inside — a shade more brilliant than Red 53A (RHS).

*Character of opening.*—The bud opens well in greenhouse.

*Effect of weather.*—In hot, dry weather, the size is slightly smaller and the color is slightly lighter than Chrysanthemum Crimson 824/1 (W).

*Sepals.*—Permanent and of medium length.

*Shape.*—Spear shaped with a wide base. When the calyx breaks, the sepals spread outwardly and then extend in a substantially horizontal manner from the calyx as the bud opens.

*Color.*—Inside — Yellow Green 146C (RHS) at the base blended to a shade slightly darker than Lavender Green 000761 (W) and Spinach Green 0960/1 (W). Outside — Spinach Green 0960/3 (W).

Peduncle:

*Size.*—Strong and erect, very long to medium in length and with medium diameter.

*Bark.*—Entirely smooth. Color: Scheeles Green 860/2 (W).

*Thorns.*—Few in number. Color: Greyed Red 182D (RHS).

*Prickles.*—Several. Color: Greyed Red 181D (RHS) becoming almost translucent at the tip.

*Hairs.*—None.

THE FLOWER

Blooming habit: Free, abundant and continuous, in greenhouse.

Size: Small — 2 to 2½ inches in diameter when fully opened.

Form: High centered, with petals at first rolled outwardly and at maturity becoming more outwardly rolled.

Borne: Several to a stem, but disbudded to one for commercial purposes, the stem being strong to medium strong and of very long length.

Petalage: Double, with 20 to 22 petals regularly arranged.

*Shape.*—Outside petals — obovate with flat apex. Intermediate petals — obovate with flat apex. Inside petals — oval with flat apex.

*Texture.*—Moderately thick and leathery.

*Aspect.*—Velvety inside surface and satiny outside surface.

Color:

A. The following is the color description of a newly opened greenhouse rose in the month of February 1977:

*Outside petals.*—Outer surface — Yellow 4B at the point of attachment blending to Yellow 4C (RHS) and to a shade slightly darker than Chrysanthemum Crimson 824/1 (W). Inside surface — Green Yellow 1B (RHS) at the point of attachment blending through Rose Red 724/1 (W) to shades of both Red 53A (RHS) and Cardinal Red 822 (W) but more brilliant and more velvet looking than either.

*Intermediate petals.*—Outside surface — Green Yellow 1C (RHS) at the point of attachment blended to Chrysanthemum Crimson 824/1 (W). Inside surface — Green Yellow 1B (RHS) at the point of attachment blending to Tyrian Rose 24 (W) and to a shade more velvet and brilliant than Red 53A (RHS).

*Inner petals.*—Outside surface — Yellow 4C (RHS) at point of attachment blending to Chrysanthemum Crimson 824 (W). Inside surface — Yellow 4B (RHS) at the point of attachment blending to Rose Red 724 (W) and to a shade slightly darker and more velvet looking than Red 53A (RHS).

B. This description was made from a rose that was open for three days in greenhouse in the month of February 1977:

*Outside petals.*—Outer surface — Green Yellow 1D (RHS) at the point of attachment blending to Yellow 8D (RHS) to Chrysanthemum Crimson 824/1 (W). Inside surface — Yellow 8C (RHS) at the point of attachment blending through Tyrian Rose 24/1 (W) to a shade more brilliant and more velvet looking than Currant Red 821 (W).

*Intermediate petals.*—Outside surface — Yellow 1D at the point of attachment blending to a shade between Red 53A and Greyed Purple 185B (RHS). Inside surface — Yellow Green 154C (RHS) at the point of attachment blending through Rose Red 724/3 (W) to a shade between Cardinal Red 822 (W) and Currant Red 821 (W) but more brilliant than either.

*Inner petals.*—Outside surface — Yellow 2C at the point of attachment blending to a shade more brilliant and brighter than Greyed Purple 185B (RHS). Inside surface — Yellow Group 2B (RHS) at the point of attachment blending to Rose Red 724/2 (W) and to a shade more brilliant and velvet looking than Crimson Red 824 (W).

*General color effect of the open bloom.*—Newly opened flower — a shade more brilliant and more velvet looking than Red 53A (RHS). Three days opened flower — a shade more brilliant and more velvet looking than Cardinal Red 822 (W).

*Frangrance.*—Very slight centifolia.

*Persistence.*—The petals hang on and dry.

*Lasting quality.*—Seven days in the month of February for cut greenhouse roses kept at living room temperatures.

REPRODUCTIVE ORGANS

Stamens: Medium in number, regularly arranged about the pistils and mixed with petaloids.

*Filaments.*—Most with anthers and the lengths vary from short to medium and long in length. Color: Yellow Green 154C at the base and becoming a transparent shade of Red 48C (RHS) under the anthers.

*Anthers.*—Medium in size and all open at once. Color: Yellow Orange 20C in the center of the pollen cuff with Greyed Orange 164B (RHS) at the margin.

*Pollen.*—Moderate in amount. Color: A shade between Yellow Orange 21B and Yellow Orange 21C (RHS).

Pistils: Many in number.

*Styles.*—Short and uneven in length, thin to moderately thin and bunched. Color: Tyrian Rose 24/2 (W) to almost transparent.

*Stigmas.*—Color — Yellow 11C (RHS).

Ovaries: Some protruding from calyx.

Hips: Short in length, globular with conspicuous neck, and moderately smooth with thick and fleshy walls.

Seeds: Few and small in size.

This new variety of rose is particularly distinguished by its very free growth habit and good wintertime productivity. Its flowers are of a lustrous red color with excellent keeping tendencies and the foliage of this plant is almost immune to mildew. This new variety of rose plant is very superior to its seed parent "Little Leaguer" in that it has increased branching and a more lustrous red color; and this plant is much superior to its pollen parent in its resistance to mildew and the occurrence of very little blind wood.

I claim:

1. A new and distinct rose plant cultivar, substantially as herein shown and described, characterized by its abundant and continuous production of lustrous red flowers, its very free growth habit with good winter productivity, and its resistance to mildew and the occurrence of blind wood.

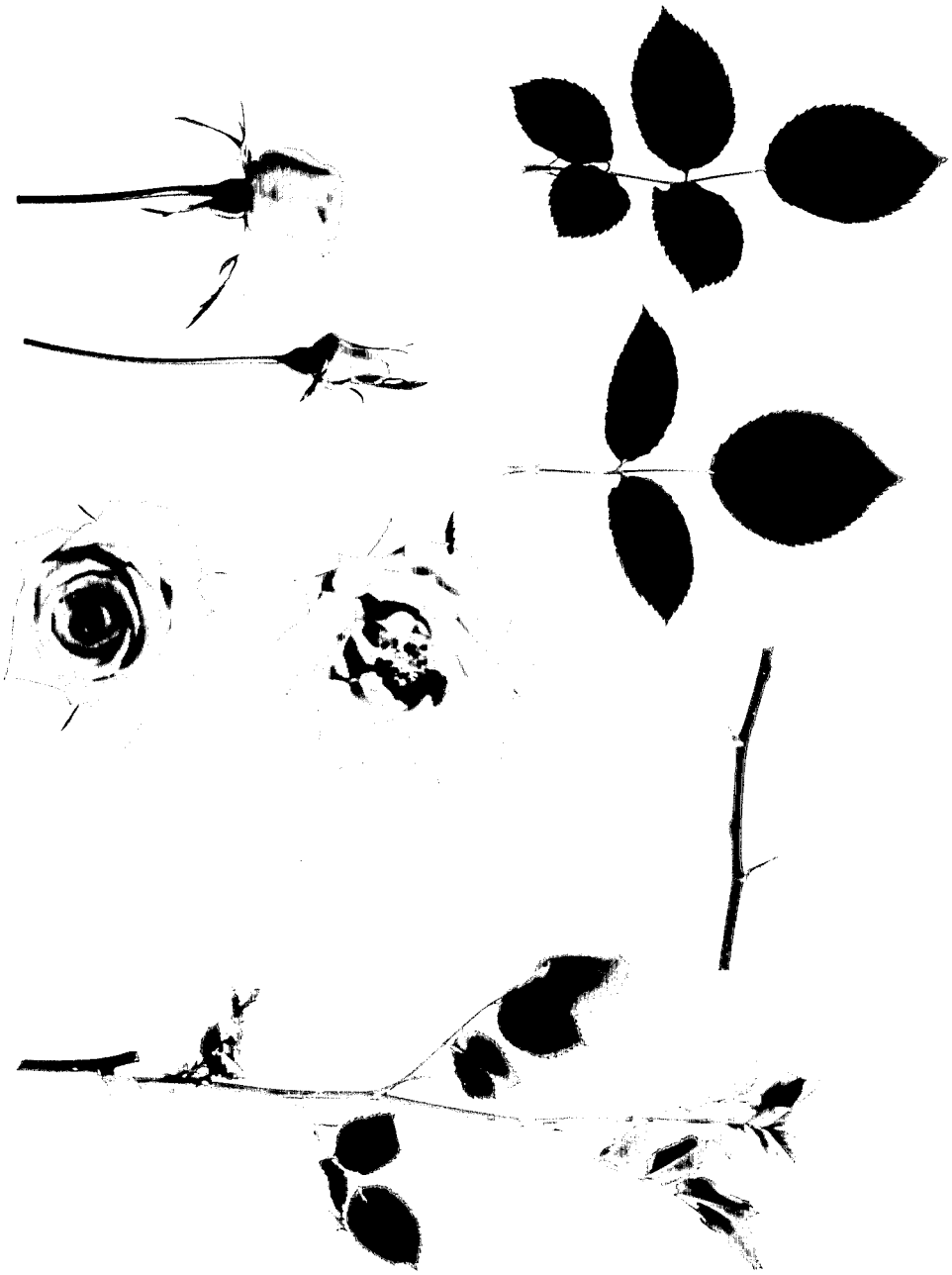

* * * * *